United States Patent [19]

Yamamoto et al.

[11] Patent Number: 4,994,414

[45] Date of Patent: Feb. 19, 1991

[54] METHOD OF PRODUCING BIOACTIVE CERAMICS CONTAINING APATITE CRYSTAL

[75] Inventors: Nobuyuki Yamamoto, Tokyo; Tsuyoshi Goto, Kanagawa; Yasunobu Horiguchi, Chiba, all of Japan

[73] Assignee: Lion Corporation, Tokyo, Japan

[21] Appl. No.: 221,527

[22] Filed: Jul. 20, 1988

Related U.S. Application Data

[63] Continuation-in-part of Ser. No. 99,784, Sep. 22, 1987, abandoned.

[30] Foreign Application Priority Data

Sep. 24, 1986 [JP] Japan .................. 61-225179
Sep. 24, 1986 [JP] Japan .................. 61-225180

[51] Int. Cl.$^5$ .................. C03C 3/097; C03G 3/078
[52] U.S. Cl. .................. 501/12; 501/32; 501/63; 501/72; 501/73
[58] Field of Search .................. 501/12, 63, 72, 73, 501/4, 32

[56] References Cited

U.S. PATENT DOCUMENTS

| | | | |
|---|---|---|---|
| 3,759,683 | 9/1973 | Dislich et al. | 501/12 |
| 3,768,432 | 10/1973 | Thomas | 501/63 |
| 3,922,155 | 11/1975 | Broemer et al. | 501/63 |
| 3,981,736 | 9/1976 | Broemer et al. | 501/73 |
| 4,324,576 | 4/1982 | Matsuyama et al. | 501/12 |
| 4,366,253 | 12/1982 | Yagi | 501/63 |
| 4,431,451 | 2/1984 | Mabia et al. | 501/12 |
| 4,605,415 | 8/1986 | Richez | 501/63 |
| 4,608,350 | 8/1986 | Howard | 501/12 |
| 4,626,514 | 12/1986 | Watanabe et al. | 501/73 |

Primary Examiner—William R. Dixon, Jr.
Assistant Examiner—David M. Brunsman
Attorney, Agent, or Firm—Burns, Doane, Swecker & Mathis

[57] ABSTRACT

A method of producing bioactive ceramics containing apatite crystal useful for artificial tooth roots or artificial bones, which comprises the steps of (i) reacting (A) at least one type of silicic acid ester such as tetramethoxysilane or tetraethoxysilane; (B) at least one type of phosphorus compound represented by general formula (II), (III), or (V):

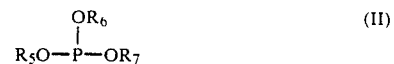

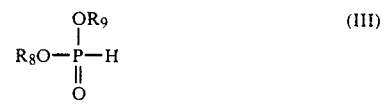

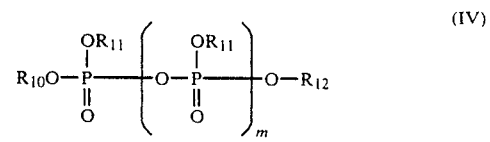

(where each of $R_5$ to $R_9$ is hydrogen, an alkyl group, with 1 to 5 carbon atoms, a phenyl radical, or an aralkyl group with 7 to 10 carbon atoms in which at least one of $R_{10}$ to $R_{12}$ is hydrogen, and m: 0 type 10); and (C) at least one water soluble calcium salt, the reaction being carried out in the presence of water at at pH of not higher than 8 to prepare a gel; and (ii) sintering the resulting gel to obtain the bioactive ceramics containing not less than 5 wt% of apatite and not more than 2wt% of Na compound as $NA_2O$.

11 Claims, No Drawings

METHOD OF PRODUCING BIOACTIVE CERAMICS CONTAINING APATITE CRYSTAL

The present application is a continuation-in-part of application Ser. No. 099,784, filed Sept. 22, 1987 now abandoned.

BACKGROUND OF THE INVENTION

(1) Field of the Invention

This invention relates to a method of producing bioactive glass or glass-ceramics which are useful for artificial tooth roots or artificial bones

(2) Prior Art

Traditionally, glass is produced by a melting method or a VAD (Vapor-Phase Axial Deposition) method, but sol-gel methods have recently become common because they enable a glass to be synthesized at a low temperature and with a high degree of purity, and because they are free from any restrictions on the range of vitrification. A sol-gel method is a method in which a metal alkoxide is hydrolyzed and polymerized so as to form a gel which is thereafter calcinated to produce glass or glass-ceramics.

Sol-gel methods which use silicon, phosphorus, and alkaline earth metal as components are unknown.

If trialkyl phosphate, which is an alkoxide of phosphorus, is used as a phosphorus component in accordance with the ordinary techniques of sol-gel methods, the hydrolyzation is so slow that unchanged trialkyl phosphate remains in the gel. Since the boiling point of trialkyl phosphate is comparatively low, the composition of the gel changes as the phosphorus component evaporates when the gel is calcinated.

If phosphoric acid is used as a phosphorus component together with an alkaline earth metal, the phosphoric acid forms salts by reacting with Ca or the like, and the salts precipitate, so that the system tends not be uniform

SUMMARY OF THE INVENTION

It is therefore an object of the present invention to provide a method of producing bioactive ceramics containing apatite crystals which are uniformly dispersed in the matrix of ceramics and which results in ceramics having good strength.

The present invention has been achieved based on the finding that, in the process of producing a silicic acid gel having as a component a water soluble calcium salt, it is possible to effectively solve the above-described problems by using a special phosphorus compound and be gelling this compound at a specific pH.

In accordance with the present invention, there is provided a method of producing a bioactive ceramics containing apatite crystal comprising the steps of (i) reacting the following components (A), (B) and (C) in the presence of water at pH of not higher than 8 so to prepare a gel comprising 20 to 70 mol % of component (A) as $SiO_2$ 1 to 50 mol % of component (B) as $P_2O_5$ and 20 to 70 mol % of component (C), wherein:

(A) is at least one of the types of silicic acid ester represented by a general formula [I]:

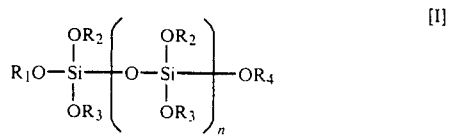

wherein each of $R_1$ to $R_4$ is hydrogen or a radical represented by $C_xH_{2x+1}(OC_2H_4)_y-$ (x: 1 to 5; y: 0 to 10), but $R_1$ to $R_4$ are not all hydrogen; and n: 0 to 20;

(B) is at least one of a phosphorus compound represented by general formulae [II], [III] or [IV]:

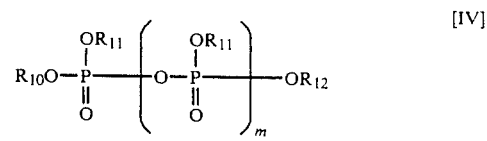

wherein each of $R_5$ to $R_{12}$ is hydrogen, an alkyl group with 1 to 5 carbon atoms, a phenyl radical, or an aralkyl group with 7 to 10 carbon atoms in which at least one of $R_{10}$ to $R_{12}$ is hydrogen; and m: 0 to 10, and (C) is at least one water soluble calcium salt; and (ii) sintering the resulting gel to obtain the bioactive ceramic containing not less than 5 wt % of apatite and not more than 2 wt % of Na compound as $Na_2O$.

In a preferred embodiment, the atomic ratio Ca/P ranges between 1.0 and 5.7 and the bioactive ceramic contains not less than 10% of apatite crystal.

DESCRIPTION OF THE PREFERRED EMBODIMENTS

Silicic acid esters (A) usable in the present invention are, preferably, those as defined by Formula [1] wherein $R_1$ to $R_4$ are $-CH_3$, $-C_2H_5$, n-$C_3H_7$, iso-$C_3H_7$, n-$C_4H_5$, or $-C_2H_4OCH_3$. More preferably, $R_1$ to $R_4$ are the same radicals selected from this list. In accordance with the present invention, silicic acid esters defined by n=0 are preferred, but condensates defined by n=1 to 10 are also preferred. Examples of silicic acid ester represented by Formula [I] are tetramethoxysilane, tetraethyoxysilane, tetra(n-propoxy)silane, tetraisopropoxysilane, tetrabutoxysilane, tetra(2-methoxyethoxy)silane, and oligomers (2 to 10 monomers) of these silicates. Of these examples, tetraethoxysilane $Si(OC_2H_5)_4$ can be readily obtained as Ethyl Silicate 28 from Colcoat Co., Ltd. and a 5-mol-average condensation product of ethyl silicate;

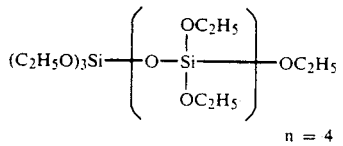

can be obtained as Ethyl Silicate 50 from Colcoat.

The concentration of the silicic acid ester in the mixture liquid can be selected as required. It may be adjusted to a level as represented by $SiO_2$ content of 0.1 to 40% by weight (hereinafter simply represented as %) or, more preferably, 2 to 30%.

Phosphorus compounds (B) usable in the present invention include a phosphorous acid itself and phosphorous acid esters as represented by Formulae [II] and [III]. Preferably, the alkyl groups in Formulae [II] and [III] have 1 to 4 carbon atoms, and phenyl radicals and benzyl radicals are also preferred. Examples of suitable compounds are those defined by Formulae [II] and [III] when $R_5$ to $R_9$ are methyl, ethyl, iso-propyl, n-propyl, butyl, phenyl, or benzyl groups.

Phosphoric acids represented by the general formula [IV] or esters of such phosphoric acids can also be usable in the present invention. One of them or a mixture of two or more of them may be selected. It is preferable to use substances defined by Formula [IV] where $m=0$ to 4. Preferably, the alkyl groups in Formula [IV] have 1 to 4 carbon atoms, and phenyl radicals and benzyl radicals are also preferred. It is possible to use, phosphoric acids in which all of $R_{10}$ to $R_{12}$ are hydrogen atoms and condensation products of these acids, and partial esters which contain both alkyl groups and hydrogen. It is most preferable to use chemical compounds as defined by Formula [IV] where at least one of $R_{10}$ to $R_{12}$ is hydrogen but, at the same time, $R_{10}$ to $R_{12}$ are not all hydrogen. Examples of these compounds are as follows:

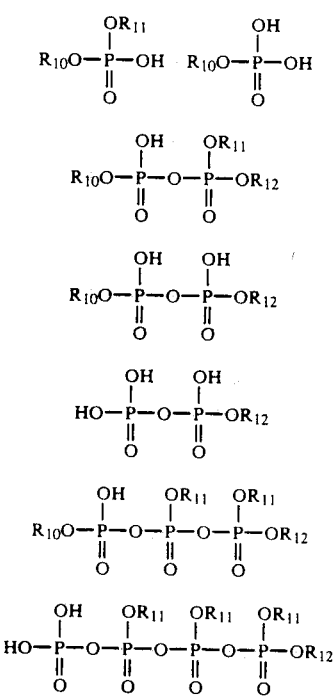

one or a mixture of two or more of these compounds are selected. In these formulas, $R_{10}$ to $R_{12}$ are the same as $R_{10}$ to $R_{12}$ in Formula [IV], except that hydrogen is excluded.

Each of the above-mentioned phosphoric acid esters can readily be obtained by a method of effecting partial hydrolysis of a corresponding phosphoric acid ester, a method of adding alcohol to a corresponding phosphoric acid and esterifying it, or a method of making phosphrous pentoxide react with alcohol and thereafter hydrolyzing it. Examples of phsophoric acid are orthophosphoric acid, pyrophosphoric acid, tripolyphosphoric acid and metaphosphoric acid. Polyphosphoric acid may be obtained by condensing orthophosphoric acid, and orthophosphoric acid is obtained by hydrolyzing phosphorus pentoxide.

Another essential component in accordance with the present invention is component (c) which is selected from at least one water soluble calcium salt. It is necessary to use a water soluble calcium salt to produce the bioactive glass or glass-ceramics of the present invention. More specifically, it is necessary to use a water soluble calcium salt in order to prepare a uniform gel which is a raw material of the sintered product. This is because calcium alkoxides are hard to dissolve in an organic solvent and are easily hydrolyzed, so that the calcium alkoxides cannot be used in case of preparing a gel containing a calcium compound in a large amount such as in the present invention. It is preferable to use calcium nitrate, calcium acetate, calcium chloride, calcium hydrogen citrate, calcium oxalate, etc.

It is essential for the present invention to form a multicomponent gel in a solution of a pH 8 or less. This is because diethyl phosphite or phosphorous acid reacts with calcium ions to cause precipitation under alkaline conditions, thereby making the system non-uniform. In addition, the same problem of the system being non-uniform is caused by the known fact that trialkyl phosphite is hydrolyzed during sol-gel reactions to form diethyl phosphite or phosphorous acid.

On the other hand, if a phosphorus compound as represented by Formula [IV] is used, calcium phosphate or hydroxyapatite may be precipitated by the reaction of phosphorus compound with calcium components if the pH exceeds 6. It is therefore suitable to form the multicomponent gel in a solution of a pH of 6 or less.

Accordingly, it is necessary for the present invention to effect the formation in a range of pH of 8 or less, wherein the phosphorus components and calcium components are mutually dissolved so as to cause uniform gelation, preferably at a pH of 6 or less or, more preferably, at a pH of 4 or less.

It is not necessary to add a pH regulating substance to the phosphorus acid, phosphoric acid, or partial esters of these acids usable in the present invention, since they are acids. It is however preferable to adjust the pH to a value within the above-described pH range if the pH deviates from the desired pH value by the influence of the kind and concentration of the calcium salt, the concentration of the phosphorus compound, or other additives.

To acidify the above aqueous solution, it is suitable to use a mineral acid such as hydrochloric acid, nitric acid, or sulfuric acid, or a organic acid such as acetic acid, citric acid or lactic acid. It is also possible to add an alkali such as aqueous ammonia in order to increase the pH. The pH of the solution may be maintained constant until gelation starts, or, in order to promote gelation, the pH may be increased to within a range which enables the maintenance of uniformity of the system.

In accordance with the present invention, it is suitable to add a quantity of a silicic acid ester represented by an $SiO_2$ content of 10 to 80 molar percent or, preferably, 20 to 70 molar percent relative to the total amount of oxides when all of the constituent elements of the gel have been converted into oxides; a quantity of a phosphorus compound represented by a $P_2O_5$ content of 0.1 to 60 molar percent or, preferably, 1 to 50 molar percent; and a quantity of the water soluble calcium salt of 10 to 80 molar percent or, preferably, 20 to 70 molar percent. In addition, it is suitable to set the atomic ratio Ca/P to within a range of 1.0 to 5.7.

A preferred content of the materials in the gel is:
$SiO_2$: 20–70 mol %
$P_2O_5$: 2–30
CaO: 25–60
Ca/P: 1.5–5.7

The content of Na is not more than 2 wt % calculated as $Na_2O$, preferably not more than 1 wt %. If the content of Na is not less than 2% calculated as $Na_2O$, the solubility of the thus produced ceramics increases and the duration of life thereof decreases at the time of implanting it into the human body.

In accordance with the present invention, it is possible to add elements other than the above constituent elements which can form constituent oxides of the gel. Example of such elements are Li, Na, K, Al, Zr, Ti, B, and so forth. These elements may also be used in the form of metal alkoxides or soluble salts. It is suitable to use each of them to a quantity defined by a content of its oxide of 0 to 20 molar percent relative to the total amount of oxides when the contents of all the constituent elements of the gel have been converted into the contents of oxides.

In this invention, there can be added fine particles or whiskers of $ZrO_2$, $Al_2O_3$, $TiO_2$, $B_2O_3$, $Y_2O_3$, SiC, $Si_3N_4$, AlN or the like singly or in combination. Furthermore, there can be added a halide such as hydrochloride, hydrofluoric acid, silicohydrofluoric acid, calcium chloride or calcium fluoride; in an amount of 0 to 10% by weight of a sulfide such as zinc sulfide; or a nucleating agent such as $La_2O_3$, $CeO_2$, $SnO_2$, $Fe_2O_3$, $Li_2O$, SrO, $Nb_2O_5$, $Ta_2O_5$, Ag, Au, Pt, Pd, Ph or the like.

The present invention produces a multicomponent gel by using the above components on the basis of, for example, the methods listed below:

(i) a method of adding a phosphorus compound to a silicic acid ester, partially hydrolyzing the silicic acid ester, and therefore adding a water soluble calcium salt, thereby completing gelation;

(ii) a method of adding a phosphorus compound after partially hydrolyzing a silicic acid ester, and then adding a water soluble calcium salt thereby completing gelation;

(iii) a method of adding a water soluble calcium salt to a silicic acid ester, adding a phosphorus compound after partially hydrolyzing the silicic acid ester, thereby completing gelation;

(iv) a method of adding a water soluble calcium salt after partially hydrolyzing a silicic acid ester, and then adding a phosphorus compound, thereby completing gelation; and (v) a method of adding a silicic acid ester to a solution of a phosphorus compound and a water soluble calcium salt, thereby effecting gelation.

The above hydrolysis and gelation by polycondensation can be effected at a room temperature, but they are also possible under a heated condition. The hydrolysis and the gelation may be effected under pressure under a heated condition and if the temperature thereof is higher than the boiling point of the solvent.

PREPARATION OF SINTERING GEL

As a method of preparing silica glasses by a sol-gel method, there is generally used a method comprising the steps of drying a gel under the condition of controlling the evaporation rate so as to form a dried gel which is free from cracks, and sintering the resulting gel by using a multiple component gel of the present invention without forming cracks in the gel. Therefore, in order to prepare a sintered gel of the multiple component gel, it is preferable to take the steps of powdering the dried gel followed by heating or the gel after heating; molding and sintering.

DRYING

The gel is dried at a temperature of 0° to 200° C. under a normal pressure or a reduced pressure. In this connection, the wet gel can be dried after being powdered or the dried gel can be powdered.

HEATING

The resulting gel is subjected to heat treatment at a temperature of not less than 200° C., preferably not less than 400° C., and lower than the temperature at which the sintering of the gel starts so as to complete the reaction occurring between components by removing the residual alcoxyl groups on the atoms of Si and P, and by promoting further the condensation polymerization of the gel. In this regard, there cannot be obtained sufficient effects by heating at a temperature of lower than 200° C.

Molding, Sintering

One of the following methods can be employed;
(i) The heated powders are molded by a single-axis press or a cold isostatic press (CIP), after which they are sintered at a temperature of 800° to 1300° C. under a normal pressure.
(ii) The heated powders are sintered at a temperature of 800° to 1300° C. by a hot-press.
(iii) The heated powders are molded, and pressed directly by a hot isostatic press, or the heated powders sintered under a normal pressure are further pressed by the hot isostatic press.

The present invention enables a silicon-phosphorus-calcium contained multicomponent gel having an uniform component distribution to be obtained easily. The gel thereby obtained can be used as a carrier for enzyme chromatography or a catalyst since it is porous and has OH radicals. It can form glass or glass-ceramics having a bio-active property when it is sintered. These materials may be effectively utilized as materials for forming artificial bones and tooth roots.

Determination of Content of Apatite Crystal Contained in Sintered Powder

The content of apatite crystal contained in the sintered product was determined by the following method:
Hydroxyapatite (sold by Dental Chemical Co., Ltd.), β-wollastonite (sold by Hayashi Kasei Co., Ltd.) and amorphous silica (sold by Nippon Aerosil Co., Ltd.) were mixed in a predetermined ratio and treated at a temperature of 1200° C. for 1 hour. Thereafter, X ray diffraction was measured on the thus treated material so as to obtain a calibration curve having a relationship between content of apatite and the strength of the diffraction peak (d−2, 72 Å) of the apatite crystal. Content of apatite of each sintered product was determined from the strength of the diffraction peak (d=2, 72 Å) thereof based on calibration curve.

REFERENCE EXAMPLE 1

9.1 g of tetramethoxysilane, 7.7 g of methanol and 10.8 g of 0.17 mol/l aqueous solution of hydrochloric acid were mixed and then violently agitated at 45° C. After 1 hour, 10.5 g of 31.3% aqueous solution of calcium nitrate was added to the mixture solution, and 3.3 g of phosphorus acid was further added. The mixture solution was then vigorously agitated, thereby obtaining a uniform solution of pH 0.8. The solution was moved into a vessel made of polypropylene and was left at rest at 45° C., and a transparent homogeneous gel was thereby obtained after 24 hours.

This gel was dried in a constant-temperature room at 45° C. for two weeks, and the molar ratio: $SiO_2/P_2O_5/CaO$ thereafter measured by using fluorescent x-ray analysis was 60/20/20. This gel was pulverized and was calcined at 1200° C. The composition of the gel was thereafter examined and the compositional ratio was found unchanged.

EXAMPLE 2

8.2 g of tetraethoxysilane, 3.6 g diethyl phosphite and 7.1 g of water were mixed and then violently agitated at 45° C. After 1 hour 18.6 g of 41.7% aqueous solution of calcium nitrate was added to the mixture solution, and this solution was further agitated vigorously for 1 hour, thereby obtaining a transparent homogeneous gel of pH 1.5.

This gel was dried in a constant-temperature room at 45° C. for two weeks, and the molar ratio: $SiO_2/P_2O_5/CaO$ thereafter measured by using fluorescent X-ray analysis was 40/13/47. This gel was pulverized heat-treated at 500 t, molded in the form of pellet by the single axis press, and sintered at 1200 t for 1 hour. The content of apatite crystal of the sintered product was determined by x-ray diffraction. The composition of the gel was thereafter examined and the compositional ratio was found The apatite crystals had the following properties:

| $SiO_2/P_2O_5/CaO$ molar ratio: | 40/13/47 |
|---|---|
| Ca/P | 1.8 |
| Formed crystal | Apatite Tricalcium phospate |
| Peak strength of apatite of x-ray diffraction(d = 2.81Å) | 800 |
| Content of apatite (wt %) | 24 |
| pH at reaction | 1.5 |

REFERENCE EXAMPLE 3

7.6 g of tetramethoxysilane, 0.65 g of trimethyl phosphite and 4.5 g of water were mixed and then vigorously agitated at 45° C. 37.5 g of 20% aqueous solution of calcium acetate was added to the mixture solution, followed by agitation. A uniform solution of pH 6.6 was thereby obtained The solution was moved into a vessel made of polypropylene and was left at rest at 45° C., and a transparent homogeneous gel was thereby obtained after about 10 minutes. This gel was dried in a constant-temperature room at 45° C. for two weeks, and the molar ratio: of $SiO_2/P_2O_5/CaO$ thereafter measured by using fluorescent X-ray analysis was 51/3/46. This gel was pulverized and was calcined at 1200° C. The composition of the gel was thereafter examined and the compositional ratio was found unchanged.

REFERENCE EXAMPLE 4

8.3 g of tetraethoxysilane, 13.2 g of triethyl phosphite and 15.4 g of 0.08 mol/l aqueous solution of hydrochloric acid were mixed and then vigorously agitated at 45° C. After 1 hour 5.2 g of 50% ethanol solution of diethoxycalcium (synthesized by the reaction of metallic calcium and ethyl alcohol) was added to the mixture solution, followed by agitation. A uniform solution of pH 3.2 was thereby obtained. The solution was transferred to a vessel made of polypropylene and was left at rest at 45° C., and a transparent homogeneous gel was thereby obtained after 48 hours.

This gel was dried in a constant-temperature room at 45° C. for two weeks, and the molar ratio: $SiO_2/P_2O_5/CaO$ thereafter measured by using fluorescent X-ray analysis was 40/39/21. This gel was pulverized and was calcined at 1200° C. The composition of the gel was thereafter examined and the compositional ratio was found unchanged.

REFERENCE EXAMPLE 5

9.0 g of Ethyl Silicate 40 (produce of Colcoat) which is condensate of ethyl silicate, 3.3 g of phosphorus acid and 10.8 g of 0.17 mol/l aqueous solution of hydrochloric acid were mixed and then vigorously agitated at 45° C. After 1 hour 10.5 g of 31.3% aqueous solution of calcium nitrate was added to the mixture solution, followed by agitation for 1 hour. A uniform solution of pH 0.70 was thereby obtained.

The solution was moved into a vessel made of polypropylene and was left at rest at 45° C., and a transparent homogeneous gel was obtained after 24 hours.

This gel was dried in a constant-temperature room at 45° C. for two weeks, and the molar ratio: $SiO_2/P_2O_5/CaO$ thereafter measured by using fluorescent X-ray analysis was 60/20/20. This gel was pulverized and was calcined at 1200° C. The composition of the gel was thereafter examined and the compositional ratio was found unchanged.

COMPARATIVE EXAMPLE 1

An experiment similar to Reference Example 4 was performed by using 14.5 g of triethyl phosphate instead of triethyl phosphite. The solution was left at rest for about 72 hours, thereby obtaining a transparent homogeneous gel. This gel was dried in a constant-temperature room at 45° C. for two weeks, and the molar ratio: $SiO_2/P_2O_5/CaO$ thereafter measured by using fluorescent X-ray analysis was 41/37/22. This gel was pulverized and was calcined at 1200° C. After compositional analysis, $SiO_2/P_2O_5/CaO=57/12/31$ was measured and a remarkable decrease in the $P_2O_5$ content was found.

COMPARATIVE EXAMPLE 2

An experiment similar to Reference Example 3 was performed by using 0.5 mol/l aqueous ammonia solution instead of water, and white precipitates were formed when an aqueous solution of calcium acetate was added. At this time, the pH was 8.2.

REFERENCE EXAMPLE 6

9.1 g of tetramethoxysilane, 7.7 g of methanol and 10.8 g of 0.17 mol/l aqueous solution of hydrochloric acid were mixed and then vigorously agitated at 45° C. After 1 hour 10.5 g of 31.3% aqueous solution of calcium nitrate was added to the mixture solution, and 4.6 g of 85% orthophosphoric acid was then added. The mixture solution was then vigorously agitated, thereby obtained a uniform solution of pH 0.4. The solution was moved into a vessel made of polypropylene and was left at rest at 45° C., and a transparent homogeneous gel was thereby obtained after 24 hours.

This gel was dried in a constant-temperature room at 45° C. for two weeks, and the molar ratio: $SiO_2/P_2O_5/CaO$ thereafter measured by using fluorescent X-ray analysis was 60/20/20. This gel pulverized and was calcined at 1200° C. The composition of the gel was thereafter examined and the composition ratio was found unchanged.

EXAMPLE 7

8.2 g of tetraethoxysilane, 30. g of 85% orthophosphoric acid and 7.1 g of water were mixed and then violently agitated at 45° C. After 1 hour 18.6 g of 41.7% aqueous solution of calcium nitrate was added to the mixture solution, and this solution was further agitated vigorously for 1 hour, thereby obtained a uniform solution of pH 1.0. The solution was moved into a vessel made of polypropylene and was left at rest at 45° C., and a transparent homogeneous gel was thereby obtained after 24 hours.

This gel was dried in a constant-temperature room at 45° C. for two weeks, and the molar ratio: $SiO_2/P_2O_5/CaO$ thereafter measured by using fluorescent X-ray analysis was 40/14/46. This gel was pulverized heat-treated at 500 t, molded in the form of pellet by the single axis press, and sintered at 1200 t for 1 hour. The content of apatite crystal of the sintered product was determined by x-ray diffraction.. The composition of the gel was thereafter examined and the compositional ratio of $SiO_2/P_2O_5/CaO$ was found unchanged.

The apatite crystals had the following properties:

| | |
|---|---|
| $SiO_2/P_2O_5/CaO$ molar ratio: | 40/14/46 |
| Ca/P | 1.6 |
| Formed crystal | Apatite Wollastonite Tricalcium phoshate Caloium pyrophosphate |
| Peak strength of apatite of x-ray diffraction(d = 2.81Å) | 400 |
| Content of apatite (wt %) | 12 |
| pH at reaction | 1.0 |

REFERENCE EXAMPLE 8

12.5 g of tetraethoxysilane, 4.6 g of 85% orthophosphoric acid and 10.8 g of 4 mol/l aqueous solution of hydrochloric acid were mixed and then vigorously agitated at 45° C. After 1 hour 16.4 g of 20% aqueous solution of calcium acetate was added to the mixture solution, thereby obtaining a solution of pH 1.5. The solution was moved into a vessel made of polypropylene and was left at rest at 45° C., and a transparent homogeneous gel was thereby obtained after 24 hours.

This gel was dried in a constant-temperature room at 45° C. for two weeks, and the molar ratio: $SiO_2/P_2O_5/CaO$ thereafter measured by using fluorescent X-ray analysis was 60.20.20. This gel was pulverized and was calcined at 1200° C. The composition of the gel was thereafter examined and the compositional ratio was found unchanged.

REFERENCE EXAMPLE 9

8.3 g of tetraethoxysilane, 7.1 g of pyrophosphoric acid and 15.4 g of 0.08 mol/l aqueous solution of hydrochloric acid were mixed and then vigorously agitated at 45° C. After 1 hour 5.2 g of 50% ethanol solution of diethoxycalcium (synthesized by the reaction of metallic calcium and ethyl alcohol) was added to the mixture solution, followed by agitation. A uniform solution of pH 2.5 was thereby obtained. The solution was moved into a vessel made of polypropylene and was left at rest at 45° C., and a transparent homogeneous gel was thereby obtained after 48 hours.

This gel was dried in a constant-temperature room at 45° C. for two weeks, and the molar ratio: $SiO_2/P_2O_5/CaO$ thereafter measured by using fluorescent X-ray analysis was 40/39/21. This gel was pulverized and was calcined at 1200° C. The composition of the gel was thereafter examined and the compositional ratio was found unchanged.

REFERENCE EXAMPLE 10

9.0 g of Ethyl Silicate 40 (product of Colcoat) which is a condensate of ethyl silicate, 3.5 g of metaphosphoric acid and 10.8 g of 0.17 mol/l aqueous solution of hydrochloric acid were mixed and then vigorously agitated at 45° C. After 1 hour 10.5 g of 31.3% aqueous solution of calcium nitrate was added to the mixture solution, followed by agitation for 1 hour. A uniform solution of pH 0.60 was thereby obtained.

The solution was moved into a vessel made of polypropylene and was left at rest at 45° C., and a transparent homogeneous gel was obtained after 24 hours.

This gel was dried in a constant-temperature room at 45° C. for two weeks, and the molar ratio: $SiO_2/P_2O_5/CaO$ thereafter measured by using fluorescent X-ray analysis was 61/19/20. This gel was pulverized and was calcined at 1200° C. The composition of the gel was thereafter examined and the compositional ratio was found unchanged.

COMPARATIVE EXAMPLE 3

An experiment similar to Reference Example 6 was performed by using 7.3 g of tirethyl phosphate instead of orthophosphoric acid. The solution was left at rest for about 72 hours, thereby obtaining a transparent homogeneous gel. This gel was dried in a constant-temperature room at 45° C. for two weeks, and the molar ratio: $SiO_2/P_2O_5/CaO$ thereafter measured by using fluorescent x-ray analysis was 61/19/20. This gel was pulverized and was calcined at 1200° C. After compositional analysis, $SiO_2/P_2O_5/CaO = 70/6/24$ was measured and a remarkable decrease in the $P_2O_5$ content was found.

EXAMPLE 11

7.1 g of 0.17 mol/l aqueous solution of hydrochlroic acid was added to 8.2 g of tetraethoxysilane, after which it was mixed at a temperature of 45° C. for 1 hour. 3.6 g of a mixture of diethyl phosphate and monoethyl phosphate (weight ratio fo diethyl phosphate/monoethyl phosphate=85/15) was added to the resulting solution, mixed for 1 hour, and 18.6 g of 41.7% aqueous solution of calcium nitrate was further added. The resulting mixture was mixed for 1 hour. The solution having pH 0.9 was transferred to a vessel made of polypropylene and was left at rest at 45° C., after which a transparent homogeneous gel was obtained after 24 hours.

This gel was dried in a constant-temperature room at 45° C. for two weeks, and the molar ratio: $SiO_2/P_2O_5/CaO$ determined by fluorescent x-ray analysis was 40/13/47. This gel was pulverized, heat-treated at 500 t, molded in the form of pellet by the single axis press, and sintered at 1200 t for 1 hour. The content of apatite crystal of the sintered product was determined by x-ray diffraction. and was calcined at 1000° C. The composition of the gel was thereafter examined and the compositional ratio of $SiO_2/P_2O_5/CaO$ was found unchanged. The apatite crystals had the following properties:

| | |
|---|---|
| $SiO_2/P_2O_5/CaO$ molar ratio: | 40/13/47 |
| Ca/P | 1.8 |
| Formed crystal | Apatite |
| Peak strength of apatite of x-ray difraction(d = 2.81Å) | 1200 |
| Content of apatite (wt %) | 35 |
| pH at reaction | 0.9 |

EXAMPLE 12

Water was added to silicic acid ester and phosphorus compound in such manner that the amount of the water was ten mole times that of the silicic acid ester, and then the resulting mixture was vigorously agitated at 45° C. After 1 hour, 50% aqueous solution of calcium nitrate was further added thereto, and a uniform solution was obtained by agitating violently the solution. Kinds of silicic acid esters and the phosphorus compounds used in this Example and the ratio of three components (the ratio being calculated by using their oxide) are shown in Table 1.

The resulting solution was then sealed in a vessel to obtain a gel by leaving the solution at rest at 45° C. for 1 night. Thereafter, the lid of the vessel was opened to dry the gel at 45° C. for 1 week. The dried gel was pulverized into powder, heated to 500° C. at a heating rate of 20° C./hr, maintained at 500° C. for 10 hours to subject it to heat treatment, further water-ground by a ball mill, and then sintered at 1200° C. for 1 hour by the hotpressing.

The composition of the resulting sintered material was determined by fluorescent X-ray analysis As a result, the analytical composition was identified with the starting composition. Rectangular bars of $3 \times 4 \times 30$ mm were cut from the resulting sintered material and the surface of the specimens was polished. Bending strength of the material was measured using a three-point bending test. The results obtained are shown in Table 1.

TABLE 1

| No. | 1 | 2 | 3 | 4 | 5 | 6 | 7 | 8 |
|---|---|---|---|---|---|---|---|---|
| $SiO_2/CaO/P_2O_5$* | 50/43/7 | 30/60/10 | 60/35/5 | 60/32/8 | 40/54/6 | 40/46/14 | 50/32/18 | 50/47/3 |
| Ca/P** | 3 | 3 | 3.5 | 2 | 4.5 | 1.7 | 0.9 | 8 |
| Silicic acid ester | tetra-ethoxy-silane | tetra-ethoxy-silane | tetra-ethoxy-silane | ethyl silicate 40 | tetra-ethoxy-silane | tetra-methoxy-silane | tetra-ethoxy-silane | tetra-ethoxy-silane |
| Phosphorus compound | monoethyl phosphate/ diethyl phosphate (50/50) | triethyl phosphite | orthophos-phoric acid | monoethyl phosphate/ diethyl phosphate (50/50) | monoethyl phosphate/ diethyl phosphate (50/50) | orthophos-phoric acid | orthophos-phoric acid | orthophos-phoric acid |
| Formed crystal | apatite wollas-tonite | apatite wollas-tonite | apatite wollas-tonite | apatite | apatite wallas-tonite | apatite tricalcium phosphate | cristoba-lite calcium pyro-phosphate | apatite wallas-tonite |
| Peak strength of apatite of x-ray diffraction (CPS) (d = 2.81Å) | 1150 | 1360 | 1000 | 1240 | 800 | 1300 | 0 | 100 |
| Content (wt %) of apatite | 34 | 40 | 29 | 37 | 24 | 38 | 0 | Trace |
| Bending Strength | 2000 | 1700 | 2200 | 1500 | 1000 | 1300 | 1000 | 1500 |
| PH at reaction | 1.2 | 0.9 | 1.0 | 1.3 | 1.0 | 0.8 | 0.7 | 1.4 |

*ratio of the components (molar ratio)
**atomic ratio

As is obvious from Table 1, in particular, Nos. 1–6 of the present invention show high bending strength, and contain large amounts of apatite crystal which are important for making chemical bonds between bones.

EXAMPLE 13

Tetraethoxysilane was used as a silicic acid ester, and gelation and heat treatment of this Example was conducted by the same method as set out in Example 12 except for the condition shown in Table 2.

The resulting dried powder was then water-ground by a ball mill, molded by a cold-isostatic press and sintered at 1200° C. under atmospheric pressure. The formed crystal is shown in Table 2.

From Table 2, it is understood that the selectivity of the crystal phase is good and large amounts of apatite crystals are formed in the case of using the partial ester of phosphoric acid as a phosphorus compound, compared with the case of using orthophosphoric acid.

TABLE 2

| No. | | 9 | 10 | 11 | 12 |
|---|---|---|---|---|---|
| *Ratio of the components | $SiO_2$ | 50 | 50 | 50 | 50 |
| | CaO | 40 | 40 | 43 | 43 |
| | $P_2O_5$ | 10 | 10 | 7 | 7 |
| Ca/P** | | 2.0 | 2.0 | 3.0 | 3.0 |
| phorsphorus compound | | monoethyl phosphate/diethyl phosphate (50/50) | orthophosphoric acid | monoethyl phosphate/diethyl phosphate (50/50) | orthophosphoric acid |
| Formed crystal | | apatite | apatite tricalcium phosphate calcium pyrophosphate | apatite wollastonite | apatite tricalcium phosphate wollastonite |
| Peak strength of x-ray diffraction (CPS) (d = 2.81Å) | | 1200 | 400 | 1100 | 600 |
| Content (wt %) of apatite | | 35 | 12 | 32 | 18 |
| PH at reaction | | 1.2 | 1.2 | 1.0 | 1.0 |

*molar ratio
**atomic ratio

EXAMPLE 14

24.3 g of 4.5 mol/l aqueous solution of hydrochloric acid was added to 25.0 g of tetraethoxysilane, after which it was mixed at a temperature of 45° C. for 1 hour. 2.4 g of a mixture of monoethyl phosphate and diethyl phosphate (weight ratio of diethyl phosphate/monoethyl phosphate=55/45) was added to the resulting solution, mixed and 55.4 g of 20% calcium acetate solution was further added thereto. The resulting solution was mixed for 1 hour and therfore pH of the solution was 2.8.

This solution was transferred to a vessel made of polypropylene and was left at rest at 60° C., after which a transparent homogeneous gel was obtained after overnight.

This gel was dried in a constant-temperature room at 60° C. for 1 week, and the molar ratio: $SiO_2/P_2O_5/CaO$ determined by fluorescent x-ray analysis was 60/4/36.

This dried gel was pulverized, heat-treated at 500° C., molded in the form of pellet by the single axis press, and sintered at 1200° C. The content of apatite crystal of the sintered product was determined by x-ray diffraction method.

The result obtained was shown in Table 3.

EXAMPLE 15

3.9 g of a mixture of monoethyl phosphate and diethyl phosphate (weight ratio of diethyl phosphate/monoethyl phosphate=55/45) was added to 21.9 g of water and then 20.8 g of tetraethoxysilane was added thereto, mixed vigorously each other at 45° C. for 1 hour, after which a homogeneous solution was obtained.

19 g of 30% calcium chloride solution was further added thereto and the solution having pH of 1.0 was obtained.

This solution was transferred to a vessel made of polypropylene and was left at rest in a constant-temperature room at 45° C., after which a transparent homogeneous gel was obtained after overnight.

This gel was dried in a constant-temperature room at 45° C. for 1 week, and the molar ratio: $SiO_2/P_2O_5/CaO$ determined by fluorescent x-ray analysis was 50/7/43.

This dried gel was pulverized, heat-treated at 500° C., molded in the form of pellet by the single axis press, and sintered at 1200° C. for 1 hour. The content of apatite crystal of the sintered product was determined by x-ray diffraction method.

The result obtained was shown in Table 3.

EXAMPLE 16

2.4 g of a mixture of monoethyl phosphate and diethyl phosphate (weight ratio of diethyl phosphate/monoethyl phosphate=55/45) was added to 24.3 g of water and then 25.0 g of tetraethoxysilane was added thereto, mixed vigorously each other at 45° C. for 1 hour, after which a homogeneous solution was obtained.

20.7 g of 50% calcium nitrate solution and 6.2 g of 20% calcium acetate solution were further added thereto and the solution having pH of 3.0 was obtained.

This solution was transferred to a vessel made of polypropylene and was left at rest in a constant-temperature room at 45° C., after which a transparent homogeneous gel was obtained after overnight.

This gel was dried in a constant-temperature room at 45° C. for 1 week, and the molar ratio: $SiO_2/P_2O_5/CaO$ determined by fluorescent x-ray analysis was 60/4/36.

This dried gel was pulverized, heat-treated at 500° C., molded in the form of pellet by single axis press, and sintered at 1200° C. for 1 hour. The content of apatite crystal of the sintered product was determined by x-ray diffraction method.

The result obtained was shown in Table 3.

TABLE 3

| Example No. | 14 | 15 | 16 |
|---|---|---|---|
| $SiO_2/P_2O_5/CaO$ molar ratio: | 60/4/36 | 50/7/4 | 60/4/36 |
| Ca/P | 4.0 | 3.0 | 4.0 |
| Formed crystal | Apatite Wollastonite | Apatite Wollastonite | Apatite Wollastonite |
| Peak strength of apatite of x-ray diffraction(d = 2.81Å) | 760 | 1100 | 500 |
| Content of apatite (wt %) | 23 | 32 | 15 |
| PH at reaction | 2.8 | 1.0 | 3.0 |

What is claimed is:
1. A method of producing a bioactive ceramics containing apatite crystal, which comprises the steps of
   (i) reacting components (A), (B) and (C) in the presence of water at pH of not higher than 8 so as to prepare a gel comprising 20 to 70 mol % of compo- nent (A) as $SiO_2$, 1 to 50 mol % of component (B) as $P_2O_5$ and 20 to 70 mol % of component (C); wherein (A) is at least one of the types of silicic acid ester represented by a general formula (I):

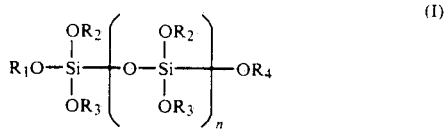 (I)

wherein each of $R_1$ to $R_4$ is hydrogen or a radical represented by $C_xH_{2x+1}(OC_2H_4)_y-$ (x: 1 to 5; y: 0 to 10); $R_1$ to $R_4$ are not all hydrogen; (and n: 0 to 20);

(B) is at least one of a phosphorus compound exclusive of phosphoric acid represented by general formulae (II), (III) or (IV):

 (II)

 (III)

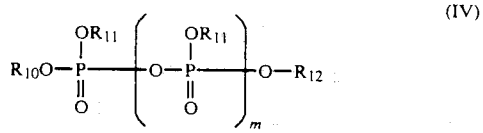 (IV)

wherein each of $R_5$ to $R_{12}$ is hydrogen, an alkyl group, a phenyl radical with 1 to 5 carbon atoms, or an aralkyl group with 7 to 10 carbon atoms; in which at least one of $R_{10}$ to $R_{12}$ is hydrogen; and m: 0 to 10, and (C) is at least one water soluble calcium salt; and (ii) sintering the resulting gel to obtain the bioactive ceramics containing not less than 5 wt % of apatite and not more than 2 wt % of Na compound as $Na_2O$.

2. A method according to claim 1, wherein each of $R_1$ to $R_4$ in Formula (I) is methyl, ethyl, n-propyl, isopropyl, n-butyl, or methoxyethyl.

3. A method according to claim 1, wherein n in Formula (I) is 0 to 10.

4. A method according to claim 1, wherein each of $R_5$ to $R_{12}$ in Formulae (II) to (IV) is hydrogen, an alkyl group with 1 to 4 carbon atoms, a phenyl radical or a benzyl radical.

5. A method according to claim 1, wherein the phosphorus compound of formula (IV) is a partial ester.

6. A method according to claim 1, wherein the pH at the reaction is equal to or lower than 6.

7. A method according to claim 1, wherein the pH at the reaction is equal to or lower than 4.

8. A method of producing a bioactive ceramics according to claim 1, wherein the ceramics contain not less than 10 wt % of apatite.

9. A method of producing a bioactive ceramics according to claim 1, wherein the ceramics contain not more than 1 wt % of Na compound as $Na_2O$.

10. A method of producing bioactive ceramics according to claim 1, wherein Ca and P are present in an atomic ratio of Ca/p of 1.0 to 5.7.

11. A bioactive ceramics containing apatite crystal prepared by the method as set forth in claim 1.

* * * * *